United States Patent [19]

Berger et al.

[11] Patent Number: 5,322,627

[45] Date of Patent: Jun. 21, 1994

[54] HIGH EFFICIENCY PACKED COLUMN SUPERCRITICAL FLUID CHROMATOGRAPHY

[75] Inventors: Terry A. Berger; William H. Wilson, both of Newark, Del.

[73] Assignee: Hewlett-Packard Company, Palo Alto, Calif.

[21] Appl. No.: 78,390

[22] Filed: Jun. 17, 1993

Related U.S. Application Data

[62] Division of Ser. No. 819,041, Jan. 10, 1992, abandoned.

[51] Int. Cl.$^5$ .............................................. B01D 15/08
[52] U.S. Cl. ................................... 210/656; 210/659; 95/82; 95/86
[58] Field of Search ............ 210/635, 656, 659, 198.2; 96/101, 104, 106; 95/82, 86

[56] References Cited

U.S. PATENT DOCUMENTS

4,479,380 6/1987 Novotny et al. .................. 210/198.2

OTHER PUBLICATIONS

Snyder, Introduction to Modern Liquid Chromatography, John Wiley & Sons, Inc., 1979, pp. 227, 228, and 238-240.
Schoenmakers et al., Trends in Anal. Chem., vol. 6, No. 1 (1987). pp. 10-17.
Supercritical Fluid Chromatography, Roger M. Smith, editor, Chapter 4, pp. 102-136, publish 1988 Royal Soc. Chem., London.
Schoenmakers, J. High Res. Chrom & Chrom. Commun. vol. 11, Mar. 1988 (pp. 278-282).
Graham et al., J. Chrom. Sci. vol. 18, Feb. 1980 pp. 75-84.
Gere, Anal. Chem. 54, 736-740 (1982).
Schwartz, LC-GC, vol. 5, No. 1 (1987) pp. 14-22.
Mourier et al., Chromatographia vol. 23, No. 1 Jan. 1987 (pp. 21-25).
Janssen et al., J. High Res. Chrom. vol. 14, Jul. 1991 (pp. 438-445).
Schoenmakers et al., Chromatographia vol. 24, 1987 (pp. 51-57).
Novotny et al., J. Chrom. 61 (1971) pp. 17-28.
Berger et al., Chromatographia vol. 30, No. ½, Jul. 1990, pp. 57-60.
Halaz et al., J. Chrom. 112 (1975) 37-60.
Kraak, et al. J. Chrom. 122 (1976) 147-158.
Dewaele, et al., J. of HRC&CC, vol. 3 (Jun. 1980) 273-276.
Journal of Chromatography vol 468, 1 Dec. 1989, pp. 127-144 T. Dean et al. 'Some Practical Aspects of Column Design, Etc.'.
Analytical Chemistry vol. 60, No. 6, 15 Mar. 1988, pp. 529-535 H. Kalinoski et al. 'Pressure Programmed Microbore Column Supercritical Fluid Chromatography, Etc.'.
Journal of High Resolution Chromatography & Chromatography Communications vol. 8, No. 12, 1 Dec. 1985, pp. 824-828 R. Christensen 'On Line Multidimensional Chromatography, Etc.'.
Journal of Chromatography vol. 477, 1 Dec. 1989, pp. 169-183 H. Engelhardt et al. 'High Performance Liquid Chromatographic Columns, Etc.'.

*Primary Examiner*—Ernest G. Therkorn
*Attorney, Agent, or Firm*—Richard F. Schuette

[57] ABSTRACT

A method and device are disclosed for performing supercritical fluid chromatography in packed columns of at least about 0.5 mm inside diameter. The column provides at least 50,000, preferably at least 100,000, theoretical plates with pressure drop across the column of at least 25 bar. The outlet pressure is controlled by the back pressure regulator. The column may comprise a plurality of individual columns in series. Separation is performed at a rate of at least 25 plates/min, preferably at least 100 plates/min.

10 Claims, 2 Drawing Sheets

5,322,627

HIGH EFFICIENCY PACKED COLUMN SUPERCRITICAL FLUID CHROMATOGRAPHY

CROSS REFERENCE TO RELATED APPLICATION

This is a divisional of application Ser. No. 07/819,041 filed on Jan. 10, 1992, now abandoned.

BACKGROUND OF THE INVENTION

This invention relates to packed-column supercritical fluid chromatography (SFC) and improvements therein.

SFC has been used in chromatographic analyses for many years. See for example T. H. Gouw et al., J. Chrom., Vol. 68, pages 303-323 (1972) using SFC in packed columns. It has also long been known to carry out SFC analyses in open-tubular or capillary columns as described in Novotny et al., U.S. Pat. No. 4,479,380.

SFC is a generic name for a type of chromatography using mobile phases that are dense gases. In SFC, the mobile phase is a fluid subjected to temperatures and pressures generally near its critical point. Fluids at those conditions have densities much closer to liquids but often exhibit greater solute diffusion characteristics than liquids. In SFC, the solvent strength changes with density and pressure drops create density and retention gradients.

Gas chromatography (GC) is in general known to exhibit very high resolving power which enables the analysis of complex materials of volatile compounds. However, only generally stable, volatile compounds can conveniently be analyzed by GC and it is not ordinarily easy to dramatically change selectivity. On occasions, some samples have been subjected to chemical derivatization to allow the use of GC. This, however, is not always a complete solution. Some compounds react more fully than others and this variable conversion rate may make the result less certain. Multiple reactions might be required to get all the solutes in a sample to be volatile and stable enough for GC. Those solutes separated, however, are not the original solutes in the sample thereby further decreasing certainty in the results.

Liquid chromatography (LC) is known to enable the analyses of labile and relatively nonvolatile compounds, but it is generally regarded to be a low resolution analytical method. There are relatively few selective or sensitive detectors that work well with the liquid mobile phases typically used in LC. As a consequence, selectivity adjustment is often used in place of efficiency to resolve components in a mixture. Often, complex samples are not easily resolved by LC. It may require a complex sample to be split into multiple parts with each part undergoing different pretreatments and analytical methods. This can be expensive and time-consuming.

SFC is often regarded as being intermediate between GC and LC. In general, packed-column SFC is superior to open-tubular SFC in achieving shorter analysis times; however, open-tubular SFC columns may provide a higher number of theoretical plates at the same pressure drop.

Many have believed that the maximum permissible pressure drop may determine when packed columns may be used for rapid analysis and when capillary columns are needed for high efficiency separations. See, for example, Novotny et al., U.S. Pat. No. 4,479,380. It has also been believed that when pressure drop across the column becomes too high it may lead to increased capacity factors and therefore to broader peaks. See Mourier et al., Chromatographia Vol. 23 No. 1 Jan. 1987 pp. 21-25. In an article by Schoenemakers et al., Chromatographic Vol. 24, pp. 51-57, 1987, the effects of column pressure drop using packed SFC columns is discussed. A plot in FIG. 1 of theoretical plate efficiency [N] versus pressure drop for three tests suggests that efficiency is at a maximum of about 25,000 plates at about 20 bar and decreases gradually at higher pressure drops above about 25 bar.

Gere, Anal. Chem. 54, 736-740 (1982), reported the use of SFC in small particle diameter packed columns at high pressure drop, for example, 184 bar in FIG. 3. However, at that pressure drop, the column efficiency was reported to be 18,750 theoretical plates.

SUMMARY OF THE INVENTION

It has been found that relatively nonvolatile and labile compounds can be rapidly separated using packed SFC columns in accordance with this invention with a combination of good sensitivity and efficiency. It is unexpected that these achievements are obtained by this invention which involves the use of a packed SFC column structure with an inside diameter of at least about 0.5 millimeter and a length sufficient to provide for at least about 50,000 theoretical plates with a pressure drop in excess of about 25 bar controlled by a back pressure regulator at the outlet. This invention is more particularly pointed out in the appended claims and described in its preferred embodiments in the following description with reference to the accompanying drawings.

DETAILED DESCRIPTION OF THE INVENTION

This invention involves the use of packed column structures for SFC which have an inside diameter (i.d.) greater than about 0.5 millimeters. The upper limit on column i.d. can vary widely with column i.d. extending to, for example, 1 meter for commercial scale chromatography as used in preparations of fine chemicals or in biotechnical engineering. The i.d. range may usually be from about 0.5 millimeters to 20 centimeters, preferably from 1 millimeter to 10 centimeters.

Figure 1:
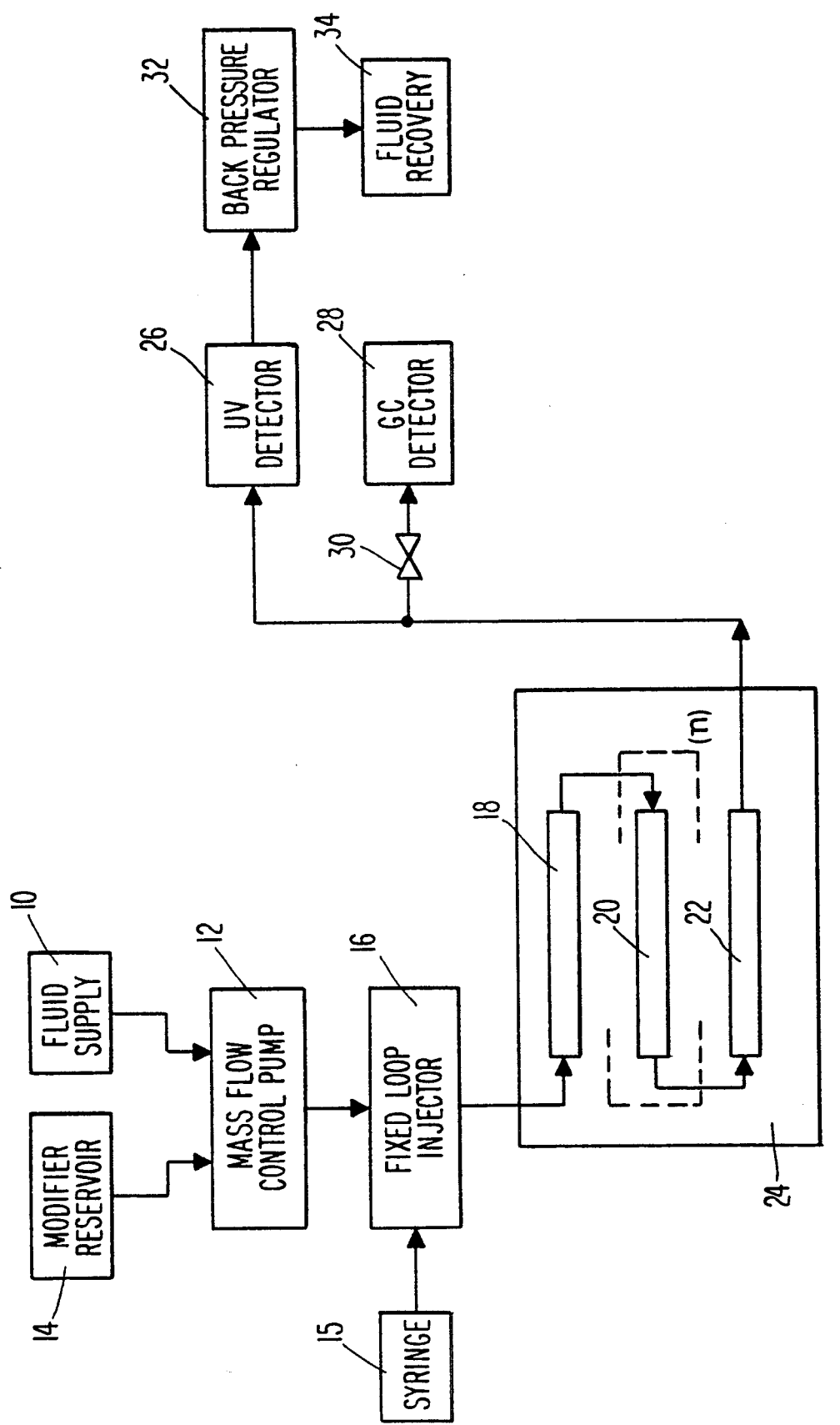
FIG. 1 is a schematic illustration of a separation system in accordance with the invention.

The column structure may be one continuous packed SFC column but preferably is made up of a plurality of individual columns connected in series as shown in FIG. 1. The number of such columns is not particularly critical but often will be between about 3 to about 20. Suitable columns are those packed columns used in LC, for example, HP ® Hypersil Column 799/6SI-574, which has an i.d. of 4.6 millimeters, a length of 200 millimeters, and is packed with silica packing material having a 5 micron average particle diameter.

The column structure is packed with a suitable SFC packing material, e.g., silica, alumina, or other known, suitable materials. The packing may be totally porous, pellicular or beads with a porous coating of a hard (nonporous) interior. Known bonded phases may be applied to the particles. The packing particles will usually have an average particle diameter between about 0.5 micron to 50 microns, preferably about 1.5 microns to 10 microns.

The length of the column structure is based on the desired number of theoretical plates which, in turn, is related to packing particle diameter. For rough calculation, the minimum single plate height (h min.) is equal to two times the average packing particle diameter (h min=2×particle diameter). For example, if a particle diameter is about 5 microns, the single plate height is about 10 microns. If a column of about 30,000 theoretical plates is desired, the length will be about 30,000×10 microns=300,000 microns=30 centimeters.

The desired number of theoretical plates should be at least 50,000 with no true upper limit but usually not much greater than about 1 million. A preferred range is about 100,000 to about 500,000 theoretical plates.

As previously pointed out this invention enables rapid separation using packed SFC columns. Separation rates of at least about 50 plates/second, preferably about 100 plates/second can be obtained. It is expected that rates of 500 plates/second or higher can be realized.

Referring now to FIG. 1, a fluid supply 10 which can be a supply of liquified compressed gas such as carbon dioxide, is connected to a mass flow control pump 12 which has a modifier reservoir 14 for the purpose of producing binary mixtures of modifier dissolved in the fluid. The pump 12 feeds the supercritical fluid at the desired mass-flow rate through fixed loop injector 16 into the inlet of individual packed SFC column 18. The sample to be separated is introduced by syringe 15 through the fixed loop injector 16. A suitable pump is a HP ® Modified Model 1050 isocratic pump. A suitable fixed loop injector is a Rheodyne Model 7410 with a microliter flow loop. Since the Model 1050 pump can ordinarily handle only one fluid at a time, two modified pumps are used, one for the fluid and the second for the modifier.

The outlet from column 18 passes into the inlet of column 20. Note that column 20 is set off in FIG. 1 by broken brackets with a subscript (n) signifying that there can be a plurality of individual columns 20 connected in series. Ordinarily, (n) may vary between about 1 to about 18 or more. The outlet of column 20 passes into the inlet of final individual column 22. The group of individual columns 18 to 22 are located within oven 24 which maintains the temperature necessary for near supercritical operation. A suitable oven is HP ® Model 5890 Chromatographic oven.

The columns used for columns 18 to 22 can be the HP ® Hypersil columns identified hereinabove. They can be identical in size and packing or they can vary in either or both respects as might be desired. For example, one could use 5 columns packed with silica and 5 columns packed with silica coated with $C_{18}$ bonded phase, or one can use columns with different internal diameters.

The outlet from final column 22 is passed to the ultraviolet (u.v.) detector 26 which produces the chromatogram. A suitable u.v. detector is HP ® Model 1050 MWD with a modified flow cell. The outlet from column 22 can also be passed to a GC detector through a fluid restrictor 30. A suitable GC detector is the flame ionization detector (FID).

The outlet from the u.v. detector 26 passes through back-pressure regulator valve 32 and from there to suitable means for fluid recovery known in the art. The back-pressure regulator 32 effectively controls the pressure throughout columns 18 to 22 such that the fluid passing from the outlet of column 22 is still at or near a desired fluid density. This insures solvation throughout the entire column structure of the series of individual columns. In accordance with this invention the pressure drop from the inlet of column 18 to the outlet of column 22 will be greater than about 25 bar, preferably between about 50 to about 400 bar.

The mobile phase can be either a fluid at or above its critical point or fluids that are subcritical but which dramatically change density when pressure is changed and change solvent strength depending on their density. This is discussed more thoroughly infra.

The mobile phase should be a single phase throughout the columns. The mobile phase can be pure or modified fluids including tertiary fluids containing additives. As examples, pure fluids include: carbon dioxide, nitrous oxide, sulfur hexafluoride, fluoroform ($CHF_3$), etc. and not limited to these. Modified fluids include: methanol, or other alcohols, acetonitrile, tetrahydrofuran, hexane and others mixed with one of the fluids mentioned under pure fluids above. Modified fluids can contain more than one modifier or more than one main fluid or both more than one modifier and more than one fluid. Tertiary fluids may include any of the mixtures under modified fluids above with the addition of polar additives such as trifluoroacetic acid, isopropylamine or a host of others mentioned in the literature. The useful concentrations of modifier are zero to approximately 50%, although higher concentrations may sometimes be useful. Additives tend to be used in much lower concentrations i.e. $10^{-5}M$ to a few percent.

Comparisons between the operation of unpacked capillary columns and the packed columns described herein are instructive in understanding this invention.

The optimum speed of a carrier gas through a chromatographic column is determined by the binary diffusion coefficient of the solute in the mobile phase and the diffusion path length in the column. Comparable diffusion path dimensions are: the inside diameter of a capillary and two times the outside diameter of packing particles. Thus, a 10 micron (i.d.) capillary column has roughly the equivalent efficiency to a packed column packed with 5 micron diameter particles. The optimum linear velocity would be the same and the number of plates per unit of length would be the same. This means that the speed and resolution would be the same. However, the amount of sample that could be injected might be very different. In a capillary, the maximum amount one can inject is proportional to the cube of the column inner diameter. Since this tends to be a very small number the amount one can inject is a very small number. A 10 micron i.d. capillary can tolerate injections no larger than a few hundred pico ($10^{-12}$) liters. On the other hand, the maximum injection volume in a packed column is not related to any dimension of a single particle. Instead, the single most important dimension is the inner diameter of the column which can be many orders of magnitude larger than the particle diameter. On a 4.6 mm I.d. packed column, for instance, at least 5 $\mu l$ (and probably 50 $\mu l$) can be injected. This is $10^4$ to $10^5$ times more volume than can be injected onto a capillary with the same efficiency per unit length. Thus, packed columns have at least the potential to detect orders of magnitude less concentrated solutes (similar mass detection but in much larger volumes).

Capillaries as narrow as 10 microns are seldom used because they are too difficult to make and use reproducibly. Instead, the most common SFC capillary is about 50 micron i.d. This column type has an optimum linear velocity 1/5th that of 5 micron packings (the diffusion path is 5 times longer so things must travel 1/5th as fast). Further, it takes a column 5 times as long to get to the same total efficiency. Thus, the typical 50 micron i.d. capillary column is 25 times slower, and up to $10^5$ times less sensitive than a packed column with the same efficiency containing 5 micron particles.

The present invention permits utilization of pre-existing components in an unexpected way. Standard columns manufactured for LC (described above) were simply connected in series using short lengths of capillary tubing. The entire stack was placed in the oven of a gas chromatograph and thermostated. Mixtures of methanol in carbon dioxide and pure carbon dioxide were used as the chromatographic mobile phases. Outlet pressure and flow rate were controlled. At 2 ml/min at the pumps, pressure drop across 11 columns (2.2 meters total length) packed with 5 micron particles was 100 to 165 bar depending on fluid temperature, pressure and composition. Temperatures from 28° to 100° C. were used although both higher and lower temperatures would be useful. Outlet pressures from 65 to 180 bar were tried but again a wider range would be useful. Flow rates were also varied from 0.5 to 4.5 ml/min (linear velocity from approximately 0.25 to 2 times optimum) and a wider range would still be useful. The fluid need not be precisely supercritical as pointed out hereinafter.

The columns produced very high efficiencies. Each column used individually produced at least about 20,000 plates using the equation for plates:

$$N = 6.28 \, (t_R/W_B)^2$$

where N is theoretical plates, $T_R$ is the retention time of a solute $W_E$ is the area/height of that same peak. This area/height measure is similar to the peak width at half height but gives a more accurate estimate of peak distortions such as tailing. Most modern recording integrators use area/height instead of peak width at half height. This difference requires a small change in the constant (6.28 instead of 5.54 used with width at half height).

Figure 2:
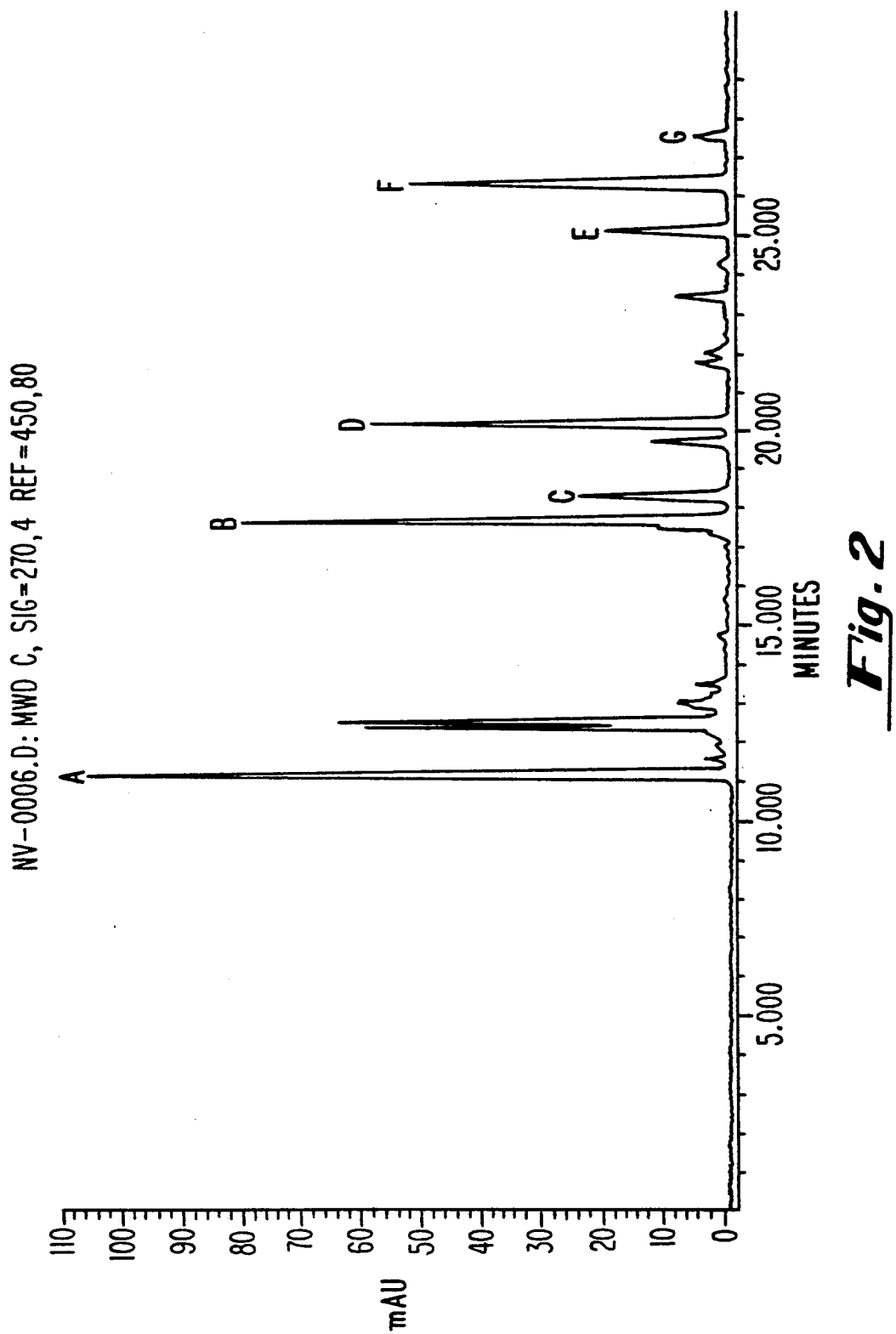
FIG. 2 is a chromatogram obtained with apparatus according to this invention.

FIG. 2 is a chromatogram obtained using 10 HP® Hypersil LC columns (described hereinabove) in series. The sample was lemon oil. The mobile phase was 5% methanol in carbon dioxide at 60° C. at 315 bar inlet pressure and 150 bar outlet pressure fed at 2 ml per minute. The fluid density in was about 0.9 and the density out was 0.8. Very sharp peaks were obtained as shown (NV-0006.D: MWDC, Sig=270, 4 Ref=450,80). Representative peaks A through G are shown in FIG. 2 and the theoretical plates were calculated using the formula $N = 6.28 \, (t_R/W_E)^2$ as follows: A=79,000 plates, B=143,000 plates, C=141,000 plates, D=164,000 plates, E=223,700 plates, F=178,000 plates, and G=257,000.

With pure carbon dioxide and modified carbon dioxide as the mobile phase, viscosity is much lower than with normal liquids. Optimum linear velocity is achieved with a flow at the pumps of 2 to 2.5 ml/min. Pressure drops averaged substantially less than 20 bar/column at these flow rates (compared to LC, ¼ the pressure drop at 3 times higher flow). At the same time efficiency was very high, averaging 100% of the theoretical. In a few isolated instances reduced plate heights as low as 1.43 have been observed. LC theories do not appear to fit packed column SFC very well.

Surprisingly, efficiency did not degrade when multiple columns were connected in series. In LC, pressure drop is very high with only a few columns in series. As more columns are used, pressure drop tends to increase until it exceeds the pressure capability of the pumping apparatus. Since the pressure drop on one column is fairly high in LC, most workers tend to avoid connecting columns in series. Those who have tried have observed serious losses in efficiency. The sum of the efficiencies of each of the LC columns used separately is much higher that the total observed efficiency of the columns connected in series. Therefore, efficiency increases more slowly than expected when the column length is increased. However, analysis time is directly proportional to the column length, so it takes longer to get relatively poorer performance.

The number of peaks that can be separated is proportional to the square root of the number of plates. This means that the number of plates must be increased by 4 times in order to separate 2 times more peaks. In LC such a doubling of the number of resolved peaks is very difficult because it requires that the column be made 4 times longer and the pressure drops tend to be excessive. The general solution has been to accept that LC is a low efficiency technique and concentrate on selectivity adjustment to resolve specific solute pairs. Complex mixtures tend to be broken down into multiple parts and each part analyzed separately.

In LC, normal phase columns are usually not very efficient, they become less efficient when they are connected in series, and the ability to increase total efficiency is very limited. In the use of SFC in this invention, none of these limitations appear to apply. Each column is extremely efficient. There is no loss in efficiency when the columns are connected in series. Pressure drops across each column are minimal. Large total pressure drops do not appear to affect peak shapes adversely. The total number of plates can be increased by at least an order of magnitude allowing more than 3 times more peaks to be separated. From the experiments conducted, it appeared likely that columns with at least 400,000 plates could be made. A typical normal phase LC column exhibits 10,000 plates which can baseline separate about 17 peaks per decade of partition ratio (k')(i.e., 16.7 peaks between k'=1 and k'=10, and 16.7 peaks between k'=10 and k'=100, etc.). With 400,000 plates one can separate 105 peaks per decade of k' (105 peaks between k'=1 and k'=10, etc.)

There is not unanimity in the art with respect to definition of the term SFC. Some workers have insisted that all subcritical operation is LC and not part of SFC. This is not always correct. There are large areas of temperature and pressure that are subcritical but the fluid behaves exactly the same as supercritical fluids. SFC is the generic name for a type of chromatography using mobile phases that are dense gases. Under International Union of Pure and Applied Chemistry (IUPAC) definitions, the fluids used are sometimes liquids and sometimes gases. However, these definitions are not very descriptive in the region of interest. The fluids can be subcritical or supercritical provided that the fluid (like carbon dioxide) acts much like a gas at high densities, using the definition of a gas as a fluid that expands to fill the volume available. The expansion is accompanied by a drop in pressure and density. A liquid is a fluid that does not expand to fill the available volume but has a characteristic volume at a specific temperature and pressure. Fluids that are near the supercritical region can be technically defined as liquids under IUPAC definitions but behave more like a gas using the above definition. Using fluids in this region results in chromatography different from LC. The most noticeable difference involves the compressibility of the fluid and the non-uniformity of the solvating power of the fluid across the column. In LC, the entire column is operated under essentially uniform conditions. The solvent strength is everywhere the same. Even in gradient elution LC where the composition of the fluid is changed vs time the rate of change is generally small enough so that the solvent strength of the mobile phase is nearly constant across the column. In SFC, the solvent strength changes with density and pressure drops create density and retention gradients. Both subcritical and supercritical fluids can create such gradients. It is this kind of behavior without losses in efficiency that applies to the process and apparatus of this invention.

Several advantages are realized in using this invention. The high efficiency of capillary GC can be achieved with the selectivity adjustment and sample capacity of LC. By using packed columns instead of capillaries, this invention permits large volume, full-loop injections to be made into a large i.d. packed SFC column, thereby eliminating the problems of poor precision and area reproducibility common with capillary columns. Large-volume injections allow lower concentrations to be detected by some detectors (e.g., mass detectors) leading to analyses with higher sensitivity. Finally, outlet pressure can be controlled using a back pressure regulator instead of a fixed restrictor as used on most capillary columns. This enables the use of pumps in the flow control mode leading to greater reproducibility of retention time over a longer period of time and operation at optimal linear velocity.

While the invention has been described and illustrated with reference to specific embodiments, those skilled in the art will recognize that modifications and variations may be made without departing from the principles of the invention as described hereinabove and as set forth in the following claims and their full range of equivalence.

We claim:

1. A method of performing the separation of material by supercritical fluid chromatography which comprises supplying fluid into the inlet of packed chromatographic column structure wherein said column structure inside diameter is at least about 0.5 millimeters, said column structure being of sufficient length between its inlet and its outlet to provide for at least about 50,000 theoretical plates, and the pressure drop from the inlet of said column structure to its outlet being at least about 25 bar, with the outlet pressure controlled by a back pressure regulator to maintain said fluid near its critical point at the outlet end of said column structure.

2. The method of claim 1 wherein the rate of said separation is at least about 50 plates per second.

3. The method of claim 1 wherein said number of theoretical plates is between about 100,000 and about 500,000.

4. The method of claim 3 wherein the rate of said separation is at least about 100 plates per second.

5. The method of claim 1 wherein said pressure drop is between about 50 bar to about 400 bar.

6. The method of claim 1 wherein said column inside diameter is between about 0.5 millimeters and about 20 centimeters.

7. The method of claim 6 wherein said inside diameter is between about 1 millimeter and about 10 centimeters.

8. The method of claim 6 wherein said column structure is packed with packing between about 0.5 microns and 50 microns in diameter.

9. The method of claim 1 wherein said column structure comprises a plurality of individual columns connected in series.

10. The method of performing the separation of material by supercritical fluid chromatography which comprises supplying fluid by means of a mass flow control pump into the inlet of a packet chromatographic column structure wherein said column packing is between about 0.5 micron and 50 microns in diameter, wherein said column structure inside diameter is between about 1 millimeter and about 10 centimeters, wherein said column structure is of sufficient length to provide for about 100,000 to about 500,000 theoretical plates, wherein the rate of said separation is at least about 100 pates per second, and the pressure drop from the inlet of said column structure to its outlet being from about 50 bar to about 400 bar, with the outlet pressure being controlled by a back pressure regulator to maintain said fluid near its critical point at the outlet of said column.

* * * * *